(12) United States Patent
Bassin et al.

(10) Patent No.: US 8,352,237 B2
(45) Date of Patent: Jan. 8, 2013

(54) SYSTEM AND METHOD FOR SYSTEM INTEGRATION TEST (SIT) PLANNING

(75) Inventors: Kathryn A. Bassin, Endicott, NY (US); Steven Kagan, Oakbrook Terrace, IL (US); Shao C. Li, Beijing (CN); Zhong J. Li, Beijing (CN); He H. Liu, Beijing (CN); Susan E. Skrabanek, Atlanta, GA (US); Hua F. Tan, Beijing (CN); Jun Zhu, Shanghai (CN)

(73) Assignee: International Business Machines Corporation, Armonk, NY (US)

( * ) Notice: Subject to any disclaimer, the term of this patent is extended or adjusted under 35 U.S.C. 154(b) by 652 days.

(21) Appl. No.: 12/558,375

(22) Filed: Sep. 11, 2009

(65) Prior Publication Data

US 2011/0066420 A1 Mar. 17, 2011

(51) Int. Cl.
*G06F 9/45* (2006.01)
(52) U.S. Cl. .......................................................... 703/22
(58) Field of Classification Search ..................... 703/22
See application file for complete search history.

(56) References Cited

U.S. PATENT DOCUMENTS

| | | | |
|---|---|---|---|
| 6,988,055 B1 | 1/2006 | Rhea et al. |
| 7,200,775 B1 | 4/2007 | Rhea et al. |
| 7,231,549 B1 | 6/2007 | Rhea et al. |
| 7,334,166 B1 | 2/2008 | Rhea et al. |
| 7,451,009 B2 | 11/2008 | Grubb et al. |
| 2006/0251073 A1 | 11/2006 | Lepel et al. |
| 2006/0265188 A1 | 11/2006 | French et al. |
| 2007/0174023 A1 | 7/2007 | Bassin et al. |
| 2008/0201611 A1 | 8/2008 | Bassin et al. |
| 2008/0201612 A1 | 8/2008 | Bassin et al. |

OTHER PUBLICATIONS

Hurlbut "Managing Domain Architecture Evolution Through Adaptive Use Case and Business Rule Models." 1997.*

* cited by examiner

*Primary Examiner* — Saif Alhija
(74) *Attorney, Agent, or Firm* — Matthew Chung; Roberts Mlotkowski Safran & Cole, P.C.

(57) ABSTRACT

A method is implemented in a computer infrastructure having computer executable code tangibly embodied on a computer readable storage medium having programming instructions. The programming instructions are operable to receive a system architecture model of a system and receive trigger coverage rules. Additionally, the programming instructions are operable to determine system integration test (SIT) coverage for each connection and interface of the system architecture model and select a set of use cases execution scenarios to satisfy the SIT coverage.

21 Claims, 11 Drawing Sheets

SYSTEM AND METHOD FOR SYSTEM INTEGRATION TEST (SIT) PLANNING

CROSS REFERENCE TO RELATED APPLICATIONS

The present invention is related to U.S. application Ser. No. 12/558,327, filed on Sep. 11, 2009; Ser. No. 12/558,274, filed on Sep. 11, 2009; Ser. No. 12/558,260, filed on Sep. 11, 2009; and Ser. No. 12/558,147, filed on Sep. 11, 2009, the contents of which are incorporated herein in their entireties by reference.

FIELD OF THE INVENTION

The present invention generally relates to system integration testing (SIT), and more particularly, to a system and method for SIT planning leveraging a system architecture model and defect reduction method (DRM) triggers.

BACKGROUND

While software systems continue to grow in size and complexity, business demands continue to require shorter development cycles. This has led software developers to compromise on functionality, time to market, and quality of software products. Furthermore, the increased schedule pressures and limited availability of resources and skilled labor can lead to problems such as incomplete design of software products, inefficient testing, poor quality, high development and maintenance costs, and the like. This may lead to poor customer satisfaction and a loss of market share for companies developing software.

To improve product quality many organizations devote an increasing share of their resources to testing and identifying problem areas related to software and the process of software development. Accordingly, it is not unusual to include a quality assurance team in software development projects to identify defects in the software product during and after development of a software product. By identifying and resolving defects before marketing the product to customers, software developers can assure customers of the reliability of their products, and reduce the occurrence of post-sale software fixes such as patches and upgrades which may frustrate their customers.

Testing and identifying problem areas related to software development may occur at different points or stages in a software development lifecycle. For example, a general software development lifecycle includes a high level requirements/design review, a detailed requirements/design review, code inspection, unit test, system test, system integration test (SIT), potentially a performance test, and typically, a user acceptance test. Moreover, as the software development lifecycle proceeds from high level requirements/design review to, for example, system integration test (SIT), performance test and user acceptance test, costs for detecting and remedying software defects generally increases, e.g., exponentially.

As such, software developers may seek to detect and remedy software defects as early in the software development lifecycle as practical in an effort to avoid the increased risks and costs of detecting and remedying these software defects later in the software development lifecycle. To aid in detecting these software defects, an organization may utilize historical defect data for a project (e.g., a software code project) in order to project future defect patterns and trends for the project.

Currently across the industry, system integration testing (SIT) is frequently performed in an ad-hoc way by running several use cases selected by human intuition rather than via a repeatable, disciplined approach. Thus, two critical factors are not typically adequately addressed in the SIT approach: (1) system architecture (including connections and interactions); and (2) an ability to empirically determine the optimal allocation of effort across different testing focuses within the system integration testing (SIT) activity. There are no industry wide models available to provide appropriate expected distributions of defects uncovered in System Integration Testing (SIT).

As a result, different testing focus areas that an effective SIT should include are rarely if ever distributed optimally. For example, many use cases actually walk through the same connection among systems/components with the same interface and data, which produces redundant test cases. Therefore, the SIT phase of the software development life cycle tends to be one of the most expensive kinds of testing relative to the benefit received. At the same time, SIT can be the most critical testing phase to ensure a successful move to production for complex system integration projects.

Accordingly, there exists a need in the art to overcome the deficiencies and limitations described herein above.

SUMMARY

In a first aspect of the invention, a method is implemented in a computer infrastructure having computer executable code tangibly embodied on a computer readable storage medium having programming instructions. The programming instructions are operable to receive a system architecture model of a system and receive trigger coverage rules. Additionally, the programming instructions are operable to determine system integration test (SIT) coverage for each connection and interface of the system architecture model and select a set of use cases execution scenarios to satisfy the SIT coverage.

In a further aspect of the invention, a system comprises a system architecture model acquisition (SAMA) tool operable to receive a system architecture model of a system and a trigger coverage rule (TCR) tool operable to receive trigger coverage rules. Additionally, the system comprises a system integration test (SIT) coverage determination tool operable to determine SIT trigger coverage for each connection and interface of the system architecture model and a use case scenario selection (UCSS) tool operable to select a set of use cases execution scenarios to satisfy the SIT trigger coverage.

In an additional aspect of the invention, a computer program product comprising a computer usable storage medium having readable program code embodied in the medium is provided. The computer program product includes at least one component operable to receive a system architecture model of a system. The system architecture model comprises a components model comprising at least one of a system, a sub system and a module of the system architecture model a connection model comprising at least one of a connection and an interface between components of the system architecture model, and one or more use case models represent business functions of the system. Additionally, the computer program product includes at least one component operable to receive trigger coverage rules and determine system integration test (SIT) coverage for each connection and interface of the system architecture model. Furthermore, the computer program product includes at least one component operable to select a minimum set of use cases execution scenarios to satisfy the SIT coverage.

In a further aspect of the invention, a computer system for determining a minimum set of use case execution scenarios to satisfy system integration test (SIT) coverage. The system comprises a CPU, a computer readable memory and a computer readable storage media. Additionally, the system comprises first program instructions to receive a system architecture model of a system. The system architecture model comprises a components model comprising at least one of a system, a sub system and a module of the system architecture model, a connection model comprising at least one of a connection and an interface between components of the system architecture model and one or more use case models represent business functions of the system. Additionally, the system comprises second program instructions to receive trigger coverage rules for one or more SIT triggers, comprising at least one of coverage, variation, sequencing and interaction. Furthermore, the system comprises third program instructions to determine system integration test (SIT) coverage for each connection and interface of the system architecture model. The system also comprises fourth program instructions to select a set of use cases execution scenarios to satisfy the SIT coverage. The first, second, third and fourth program instructions are stored on the computer readable storage media for execution by the CPU via the computer readable memory.

BRIEF DESCRIPTION OF THE SEVERAL VIEWS OF THE DRAWINGS

The present invention is described in the detailed description which follows, in reference to the noted plurality of drawings by way of non-limiting examples of exemplary embodiments of the present invention.

DETAILED DESCRIPTION

Figure 1:
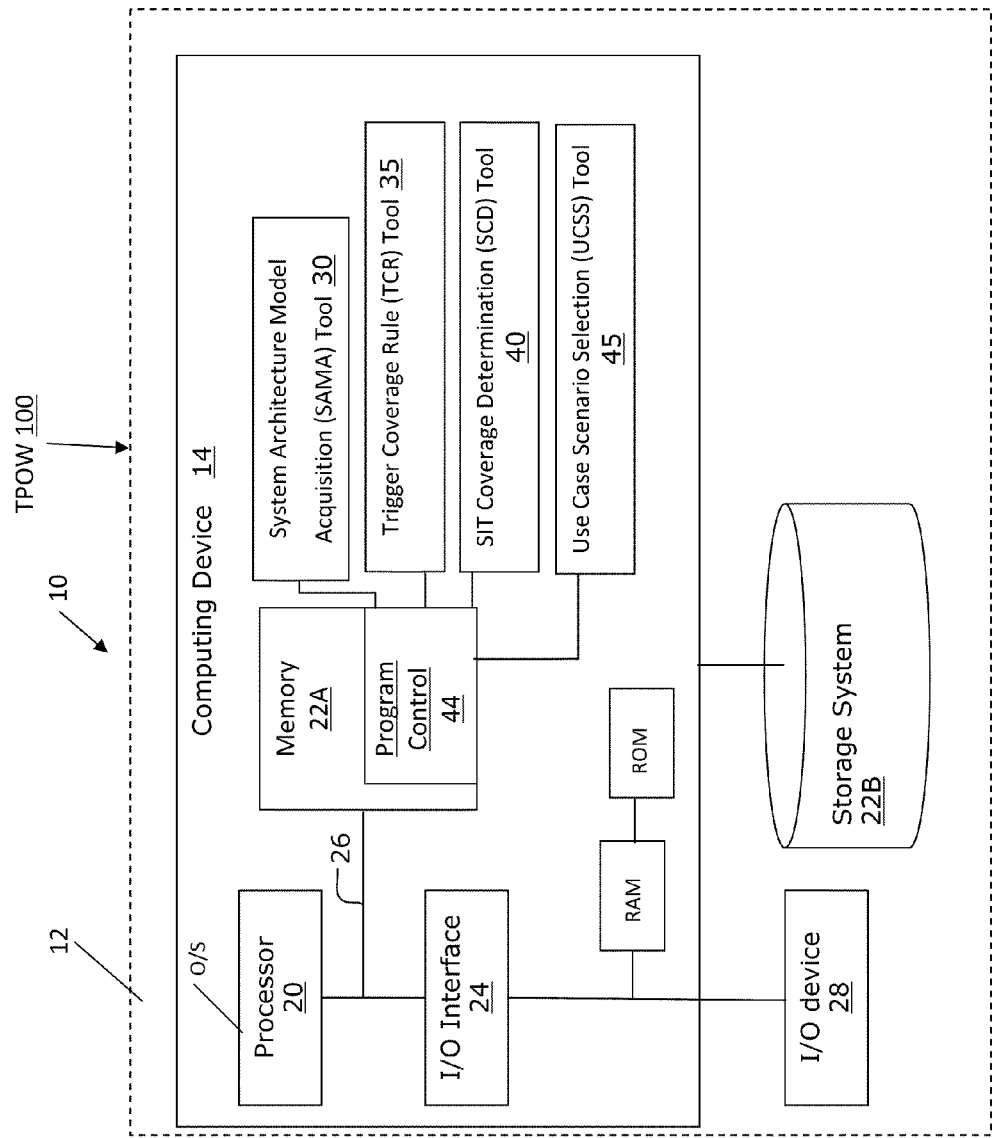
FIG. 1 shows an illustrative environment for implementing the steps in accordance with aspects of the invention.

The present invention generally relates to system integration testing (SIT), and more particularly, to a system and method for SIT planning leveraging a system architecture model and defect reduction method (DRM) triggers. The present invention is operable to derive an optimized and achievable SIT allocation of effort strategy consistently and accurately across any system integration effort, regardless of size, complexity, or industry. The present invention incorporates elements of (1) the system architecture and (2) the defect reduction method (DRM) to optimize the distribution of test cases for SIT efforts.

Implementing the present invention enables a significant reduction of overall testing costs while simultaneously improving test quality, for example, for complex system integration clients. For example, the present invention provides appropriate expected defect distributions of SIT in order for an organization to effectively address such defects, e.g., optimize the distributions of SIT test case focus areas. The present invention is operable to determine SIT test case focus areas regardless of project size, complexity or industry.

The present invention provides a consistent model for optimizing SIT that offers significant advantages over the conventional ad-hoc approach. For example, with the present invention the system architecture information is leveraged in a way that ensures the critical interaction/connection scenarios will be covered while conducting the SIT. Additionally, empirical guidance around DRM trigger distributions are leveraged in a way to ensure that the SIT is adequately balanced and/or thorough. Implementing a systematic model enables accurate forecasting at substantially earlier points in the software development life cycle than would otherwise be feasible, which enables significant cost savings.

In embodiments, the present invention further provides a SIT planning method (and apparatus implementing a method) comprising steps to derive the optimal SIT testing design. In embodiments, the overall system component/connection/interface information, as well as the mapping relationship from use case scenarios to the system architecture are acquired. The desired coverage rules for the applicable SIT triggers for each connection/interface is determined based on, for example, best practice standards for that industry and/or a client's own historical data, (e.g., at the client's option). The needed SIT coverage is determined for each connection and interaction of the system, including, for example, how many simple, variant, sequence, interaction and/or workload/stress testing occurrences should be executed for each connection and interaction of the system, in accordance with the coverage rules determined in the prior step. A minimum set of use cases execution scenarios to satisfy the coverage goal is generated, and then use the minimum set of use cases execution scenarios to support the generation of SIT testing design guidelines, as explained below.

System Environment

As will be appreciated by one skilled in the art, the present invention may be embodied as a system, method or computer program product. Accordingly, the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present invention may take the form of a computer program product embodied in any tangible medium of expression having computer-usable program code embodied in the medium.

Any combination of one or more computer usable or computer readable medium(s) may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following:

an electrical connection having one or more wires,
a portable computer diskette,
a hard disk,
a random access memory (RAM),
a read-only memory (ROM),
an erasable programmable read-only memory (EPROM or Flash memory),
an optical fiber,
a portable compact disc read-only memory (CDROM), an optical storage device,
    a transmission media such as those supporting the Internet or an intranet, or
    a magnetic storage device.

The computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, etc.

Computer program code for carrying out operations of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network. This may include, for example, a local area network (LAN) or a wide area network (WAN), or the connection may be made to an external computer (for example, through the Internet using an Internet Service Provider).

FIG. 1 shows an illustrative environment 10 for managing the processes in accordance with the invention. To this extent, the environment 10 includes a server or other computing system 12 that can perform the processes described herein. In particular, the server 12 includes a computing device 14. The computing device 14 can be resident on a network infrastructure or computing device of a third party service provider (any of which is generally represented in FIG. 1). In embodiments, the environment 10 may be designated as a test planning optimization workbench (TPOW) 100.

The computing device 14 includes a system architecture model acquisition (SAMA) tool 30 operable to acquire the overall system component/connection/interface information, as well as the mapping relationship from use case scenarios to the system architecture. For example, the SAMA tool 30 is operable to identify, capture and/or refine system architecture models. Additionally, the SAMA tool 30 is operable to map system level connections with use case scenarios annotated via the trigger based "sequence" and "interaction" relationships, as explained further below. Additionally, the computer device 14 includes a trigger coverage rule (TCR) tool 35 operable to determine the desired coverage rules for the applicable SIT triggers for each connection/interface based on, for example, best practice standards for a particular industry and/or a client's own historical data, (e.g., at the client's option). For example, the TCR tool 35 is operable to apply test coverage rules to systematically capture experience and/or knowledge, as explained below. In accordance with aspects of the invention, this experience and/or knowledge can be applied and reused in a risk-based way.

The computer device 14 also includes a SIT coverage determination (SCD) tool 40 operable to determine the needed system integration testing (SIT) coverage (e.g., risk/rule based test case execution requirements) for each connection and interaction of the system. This determination includes, for example, how many simple, variant, sequence, interaction and/or workload/stress testing occurrences (e.g., test case execution requirements) should be executed for each connection and interaction of the system, in accordance with the coverage rules determined by the TCR tool 35. Additionally, the computer device 14 includes a use cases scenario selection (UCSS) tool 45 operable to generate a minimum set of use cases execution scenarios to satisfy the coverage goal and generate SIT testing design guidelines using the minimum set of use cases execution scenarios. In embodiments, the UCSS tool 45 is operable to combine coverage goals and the type of testing to extrapolate the minimum set of use case execution scenarios while accounting for desired risk levels, as explained below. The SAMA tool 30, the TCR tool 35, the SCD tool 40 and the UCSS tool 45 can be implemented as one or more program code in the program control 44 stored in memory 22A as separate or combined modules.

The computing device 14 also includes a processor 20, memory 22A, an I/O interface 24, and a bus 26. The memory 22A can include local memory employed during actual execution of program code, bulk storage, and cache memories which provide temporary storage of at least some program code in order to reduce the number of times code must be retrieved from bulk storage during execution. In addition, the computing device includes random access memory (RAM), a read-only memory (ROM), and an operating system (O/S).

The computing device 14 is in communication with the external I/O device/resource 28 and the storage system 22B. For example, the I/O device 28 can comprise any device that enables an individual to interact with the computing device 14 or any device that enables the computing device 14 to communicate with one or more other computing devices using any type of communications link. The external I/O device/resource 28 may be for example, a handheld device, PDA, handset, keyboard etc.

In general, the processor 20 executes computer program code (e.g., program control 44), which can be stored in the memory 22A and/or storage system 22B. Moreover, in accordance with aspects of the invention, the program control 44 controls the SAMA tool 30, the TCR tool 35, the SCD tool 40 and the UCSS tool 45. While executing the computer program code, the processor 20 can read and/or write data to/from memory 22A, storage system 22B, and/or I/O interface 24. The program code executes the processes of the invention. The bus 26 provides a communications link between each of the components in the computing device 14.

The computing device 14 can comprise any general purpose computing article of manufacture capable of executing computer program code installed thereon (e.g., a personal computer, server, etc.). However, it is understood that the computing device 14 is only representative of various possible equivalent-computing devices that may perform the processes described herein. To this extent, in embodiments, the functionality provided by the computing device 14 can be implemented by a computing article of manufacture that includes any combination of general and/or specific purpose hardware and/or computer program code. In each embodiment, the program code and hardware can be created using standard programming and engineering techniques, respectively.

Similarly, the computing infrastructure 12 is only illustrative of various types of computer infrastructures for implementing the invention. For example, in embodiments, the server 12 comprises two or more computing devices (e.g., a server cluster) that communicate over any type of communications link, such as a network, a shared memory, or the like, to perform the process described herein. Further, while performing the processes described herein, one or more computing devices on the server 12 can communicate with one or more other computing devices external to the server 12 using any type of communications link. The communications link can comprise any combination of wired and/or wireless links; any combination of one or more types of networks (e.g., the Internet, a wide area network, a local area network, a virtual private network, etc.); and/or utilize any combination of transmission techniques and protocols.

Flow Diagrams

FIGS. 2, 3, 5-7, 10 and 11 shows exemplary flows for performing aspects of the present invention. The steps of FIGS. 2, 3, 5-7, 10 and 11 (and any other figures that show underlying functionality of the system) may be implemented in the environment of FIG. 1, for example. The flow diagrams may equally represent high-level block diagrams or swim-lane diagrams of the invention. The flowcharts and/or block diagrams in FIGS. 2, 3, 5-7 and 9-11 illustrate the architecture, functionality, and operation of possible implementations of systems, methods and computer program products according to various embodiments of the present invention. In this regard, each block in the flowcharts, block diagrams or swim-lane diagrams may represent a module, segment, or portion of code, which comprises one or more executable instructions for implementing the specified logical function(s). It should also be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. Each block of each flowchart, and combinations of the flowchart illustration can be implemented by special purpose hardware-based systems that perform the specified functions or acts, or combinations of special purpose hardware and computer instructions and/or software, as described above. Moreover, the steps of the flow diagrams may be implemented and executed from either a server, in a client server relationship, or they may run on a user workstation with operative information conveyed to the user workstation. In an embodiment, the software elements include firmware, resident software, microcode, etc.

In embodiments, a service provider, such as a Solution Integrator, could offer to perform the processes described herein. In this case, the service provider can create, maintain, deploy, support, etc., the computer infrastructure that performs the process steps of the invention for one or more customers. These customers may be, for example, any business that uses technology. In return, the service provider can receive payment from the customer(s) under a subscription and/or fee agreement and/or the service provider can receive payment from the sale of advertising content to one or more third parties.

Furthermore, the invention can take the form of a computer program product accessible from a computer-usable or computer-readable medium providing program code for use by or in connection with a computer or any instruction execution system. The software and/or computer program product can be implemented in the environment of FIG. 1. For the purposes of this description, a computer-usable or computer readable medium can be any apparatus that can contain, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable storage medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disc-read/write (CD-R/W) and DVD.

Figure 2:
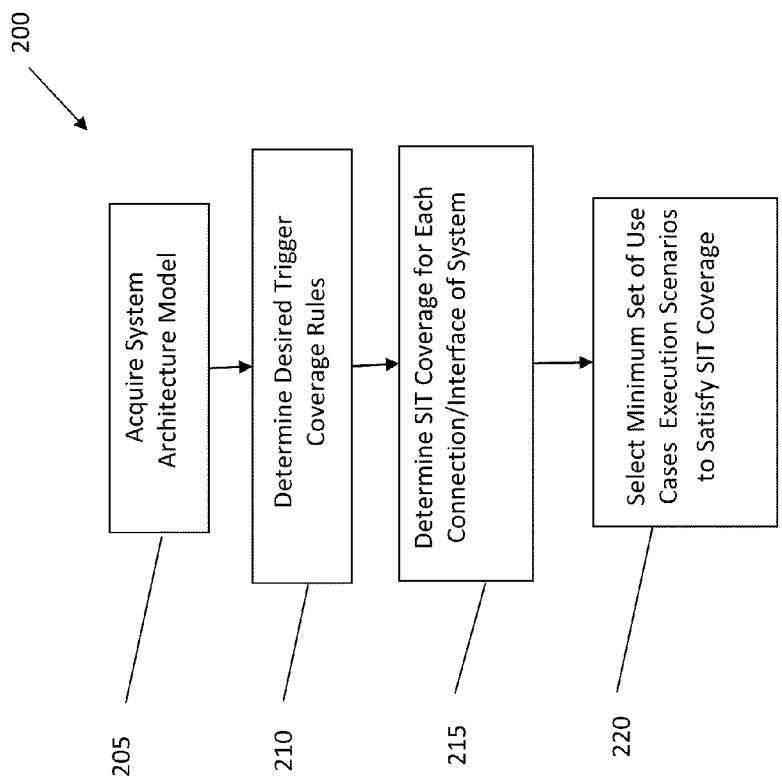
FIGS. 2 and 3 show exemplary flow diagrams in accordance with aspects of the invention.

FIG. 2 depicts an exemplary flow 200 for process in accordance with aspects of the present invention. As shown in FIG. 200, at step 205, the SAMA tool 30 acquires the overall system component/connection/interface information, as well as the mapping relationship from use case scenarios to the system architecture (i.e., step 1). The details of step 205 are described below with reference to FIGS. 3-5. At step 210, the TCR tool 35 determines the desired coverage rules for the applicable SIT triggers for each connection/interface (i.e., step 2). This determination may be based on, for example, best practice standards for a particular industry and/or a client's own historical data, (e.g., at the client's option). The details of step 205 are described below with reference to FIG. 6.

At step 215, the SCD tool 40 determines the needed SIT coverage for each connection and interaction of the system (i.e., step 3). This determination includes, for example, how many simple, variant, sequence, interaction and workload/stress testing occurrences should be executed for each connection and interaction of the system, in accordance with the coverage rules determined by the TCR tool 35. The details of step 215 are described below with reference to FIGS. 7-9. At step 220 the UCSS tool 45 generates a minimum set of use cases execution scenarios to satisfy the coverage goal and generates SIT testing design guidelines using the minimum set of use cases execution scenarios (i.e., step 4). The details of step 220 are described below with reference to FIGS. 10 and 11.

System Architecture Model Acquistion and Method

In accordance with aspects of the invention, the system architecture model acquisition tool 30 is operable to acquire the overall system architecture (e.g., component, connection and/or interface information), as well as a mapping relationship from use case scenarios to the system architecture. For example, the SAMA tool 30 is operable to identify, capture and/or refine system architecture models. Additionally, the SAMA tool 30 is operable to map system level connections with use case scenarios annotated via the trigger based "sequence" and "interaction" relationships, as explained further below. By acquiring the overall system architecture and mapping relationships from use case scenarios to the system architecture, the present invention enables an SIT to be optimized to focus efforts on important aspects of the system architecture.

Figure 3:
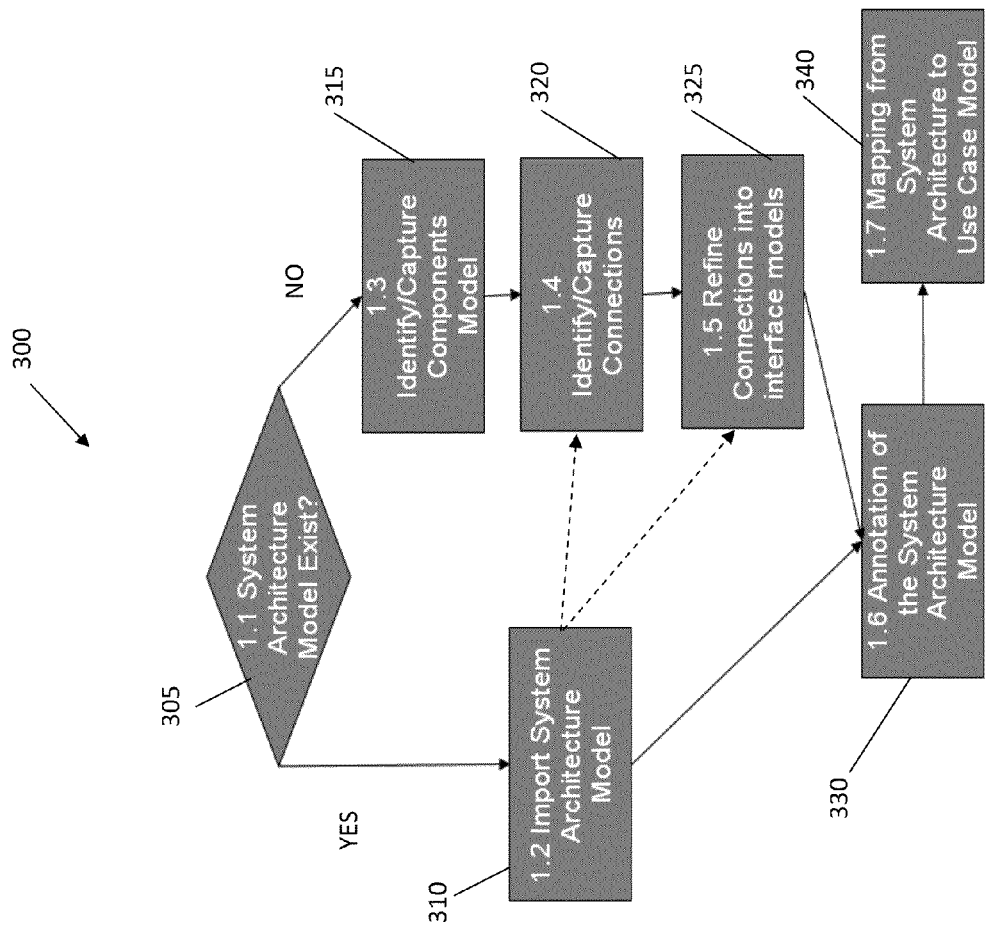

FIG. 3 shows an exemplary flow diagram 300 for system architecture model acquisition in accordance with aspects of the invention. The numbers designated in each flow should not be interpreted as having to be performed in the sequence provided, as discussed above, and should not be considered a limiting feature. As shown in FIG. 3, at step 305, the SAMA tool determines whether an existing system architecture model is available, e.g., in a database (for example, storage system 22B shown in FIG. 1) but in some other format (e.g., UML Diagram, spreadsheet, etc.) and/or of sufficient quality. If, at step 305, the SAMA tool determines that an existing system architecture model is available, at step 310, the SAMA tool imports the system architecture model. The format of the system architecture model (e.g., UML Diagram, spreadsheet, etc.) enables the SAMA tool to extract the system architecture model information and map the system architecture model elements into TPOW system architecture model elements. In embodiments, the SAMA tool may utilize mapping of terminology to establish the linkage between the two meta-models (e.g., UML Diagram, spreadsheet and the TPOW system architecture model elements).

If, at step 305, the SAMA tool determines that an existing system architecture model is not available, at step 315, the SAMA tool identifies and/or captures high level components model of the system architecture. As should be understood by those of ordinary skill in the art, "component" may be a system, sub-system and/or a system module, amongst other components. At step 320, the SAMA tool identifies and/or captures the connection model of the system architecture model. For example, if one component has any functional dependency over another component, such functional dependency should be represented by a connection between the two components.

At step 325, the SAMA tool refines the connection model into a finer level of granularity interface model. For example, one or more of the connections may include several interfaces to represent the actual interaction between components. As shown in FIG. 3, subsequent to step 310, the SAMA tool may optionally (as represented by the dashed lines) proceed to step 320 or step 325 to further refine the imported system architecture model.

Following either step 310 or step 325, at step 330, the SAMA tool annotates the system architecture model for capturing, for example, interface/interface relationship and/or connection exception numbers (or, the potential error types that can occur during the integration related to data issues, network problems, etc.) The SAMA tool is operable to capture interface/interface relationships e.g., sequence relationships and/or interaction relationships. With a sequence relationship, the interface invocations are usually performed in a sequenced manner. In contrast, with an interaction relationship, the interface invocations are usually performed in parallel with potential conflicts.

At step 340, the SAMA tool maps the system architecture model with the function model (e.g., a use case model) of the solution (e.g., the optimized SIT plan) determined by the TPOW 100. A use case may be used, for example, during a low level design phase of the software development life cycle to translate requirements (for example, "must do X but not allow Y") for the software project (e.g., determined during the requirements phase of the software development life cycle) into use case scenarios. Additionally, the SAMA tool may import use case models, for example, from other requirement management systems. In embodiments, each use case scenario may be associated with one or more modeling elements in the system architecture model (with different levels of granularity as may be needed), including, for example, components, connections, and/or interfaces. In accordance with aspects of the invention, the SIT test cases (e.g., "if passes test, then okay, if fails test, then defect") are based upon the use case scenarios. As explained below, the TPOW 100 utilizes the use case scenarios to select optimized test cases (or test case suites) for SIT.

TABLE 1 shows exemplary system architecture model elements utilized by the TPOW in accordance with aspects of the invention.

TABLE 1

| Architecture Model Element: | Description: |
| --- | --- |
| Component | Can be, e.g., system, sub-system, module |
| Connection | Function dependency between components |
| Interface | Representing different function invocation in a connection |
| Interface Relationship | Sequence and interaction |
| Use Case Mapping | Linking business function to system architecture elements |

Figure 4:
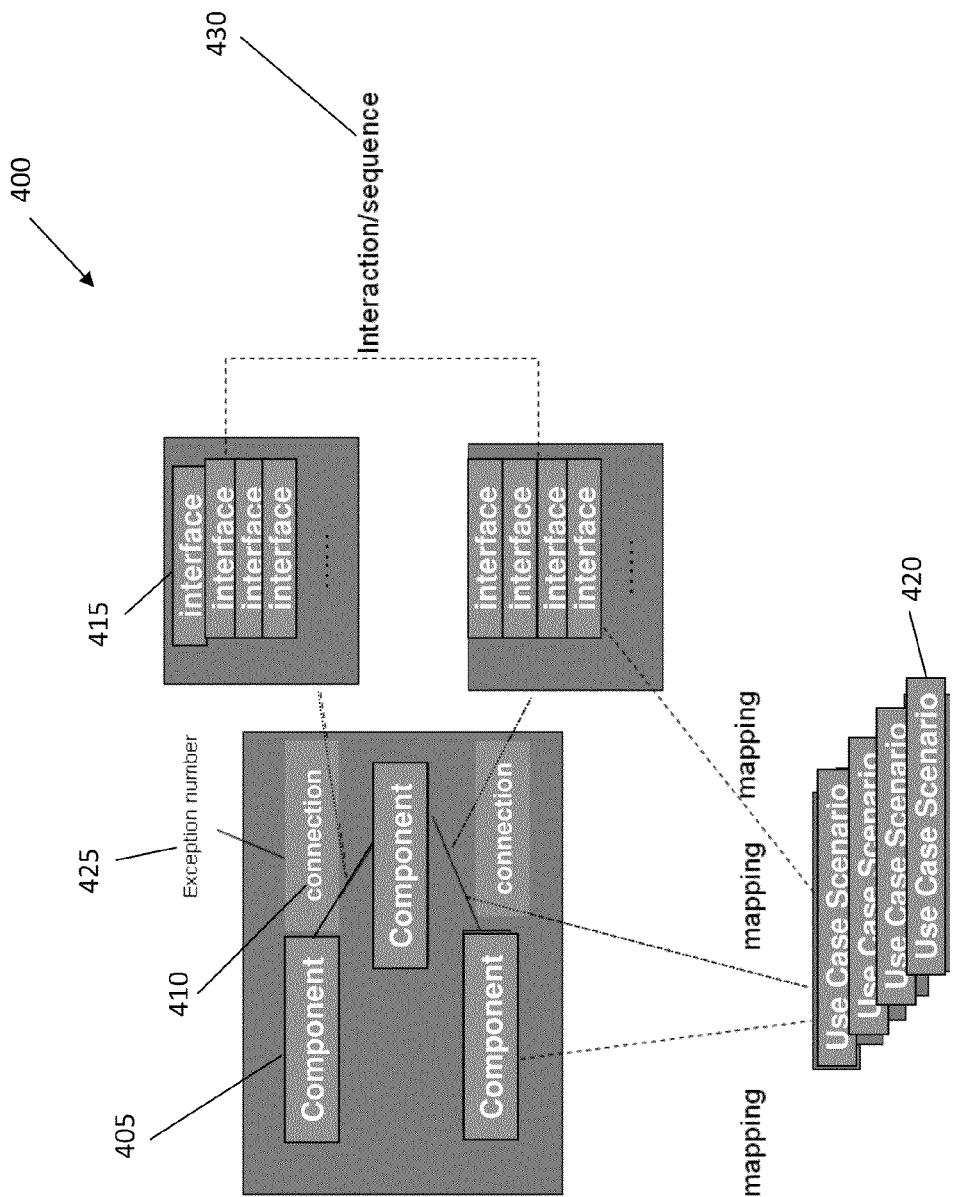
FIG. 4 shows an exemplary system architecture model in accordance with aspects of the invention.

FIG. 4 shows an exemplary system architecture model 400 used to describe the present invention. The SAMA tool 30, performing the steps illustrated in FIG. 3, may determine the system architecture model 400. As should be understood, the invention contemplates any number of system architecture models being possible. As shown in FIG. 4, the exemplary system architecture model 400 includes a plurality of components 405 with connections 410 (e.g., senders of information) between components 405. Additionally, some of these connections 410 may be interfaces 415, which may be more complex than connections (e.g., logic controlled senders of information).

FIG. 4 also shows annotations of the system architecture model for capturing, for example, interface/interface relationships 430 and/or connection exception numbers 425. These annotations (e.g., the connection exception numbers 425 and the interface/interface relationships 430) represent the potential error types that can occur during the system integration testing (SIT), for example, related to data issues, network problems, etc., as explained below. Additionally, FIG. 4 illustrates a plurality of use case scenarios 420, which may be used in accordance with aspects of the invention to determine test cases, as explained below.

Figure 5:
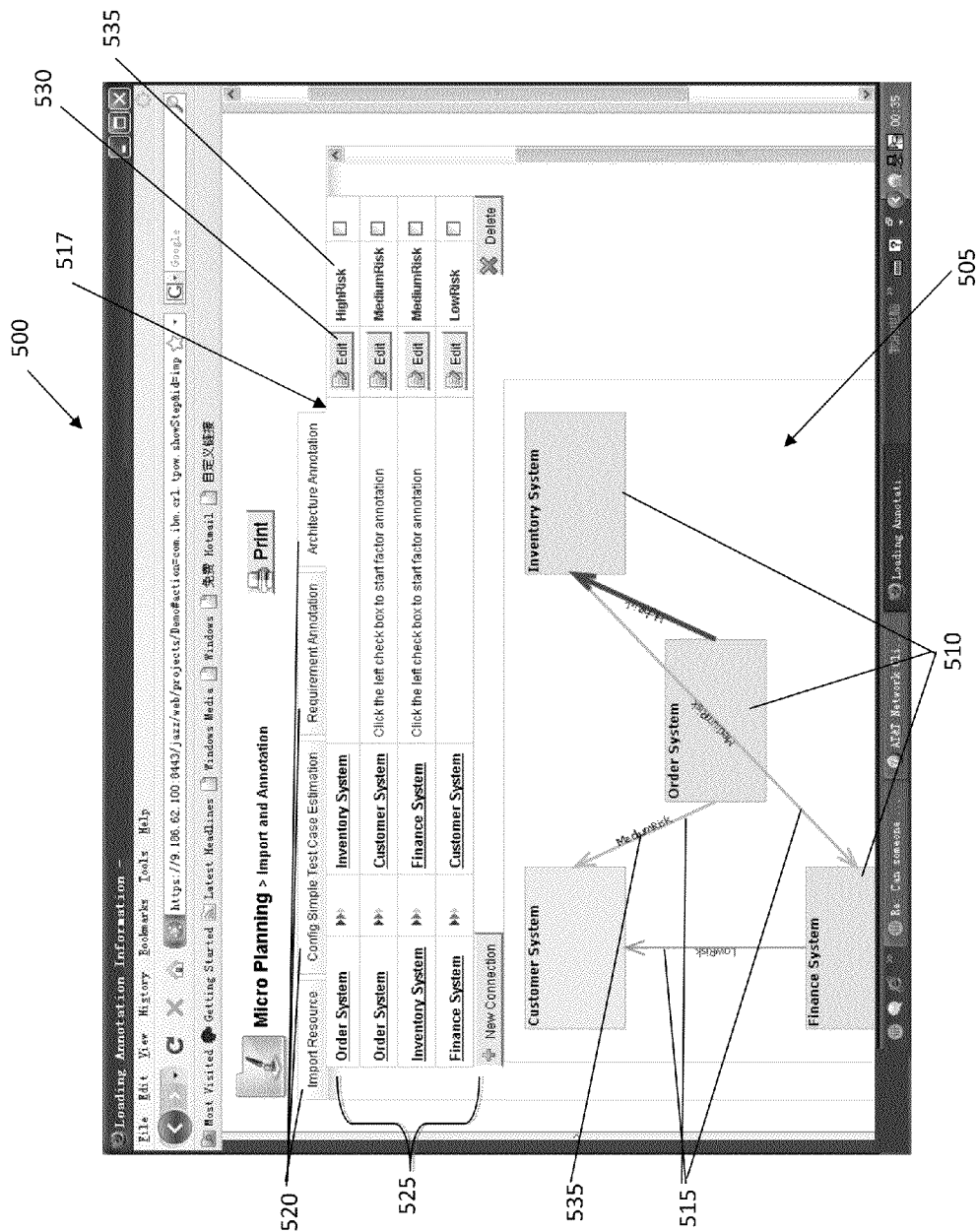
FIG. 5 illustrates an exemplary user interface and underlying functionality in accordance with aspects of the invention.

FIG. 5 illustrates an exemplary user interface 500 of the test planning optimization workbench TPOW 100 for constructing, viewing, and editing a given system architecture model 505. As should be understood, the invention contemplates other user interfaces may be utilized with the present invention. Additionally, the user interface 500 includes tabs 520 for aspects (e.g., import resource, configure simple test case estimation, requirement annotation and architecture annotation (selected)) of the user interface 500. As shown in FIG. 5, the system architecture model 505 includes components 510 (e.g., finance system, order system, customer system and inventory system) and connections 515 (some of which may be interfaces) between the components 510. Additionally, the user interface 500 includes table 517, which includes lists 525 of each of the connections 515 between the components 510. Additionally, table 517 includes edit buttons 530 for each of the connections and a risk level 535 (e.g., high, medium or low, amongst other risk levels). The risk levels 535 for each of the connections 515 of a system architecture model 505 may be determined as disclosed in related U.S. application Ser. No. 12/558,147, filed on Sep. 11, 2009.

Trigger Coverage Determination and Method

Figure 6:
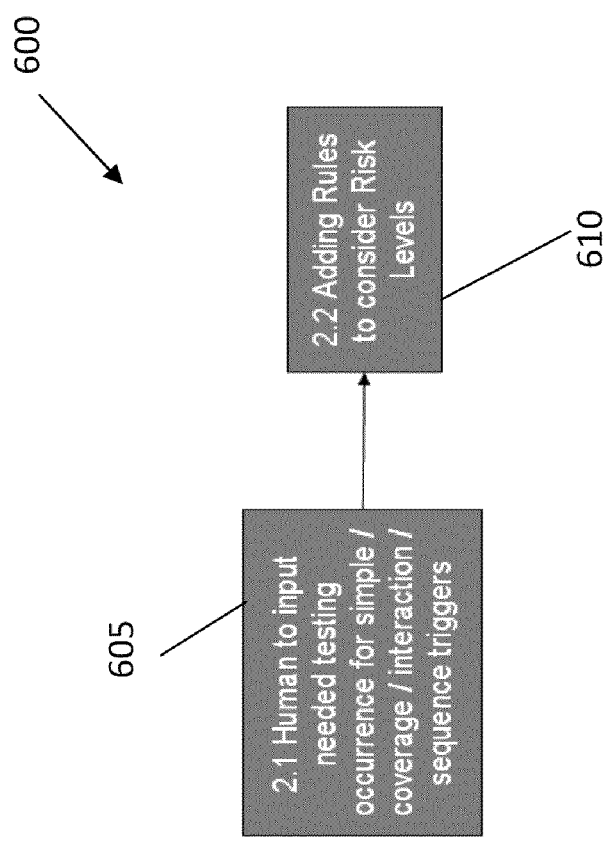
FIGS. 6 and 7 show exemplary flow diagrams in accordance with aspects of the invention.

FIG. 6 show an exemplary flow 600 for determining trigger coverage in accordance with aspects of the invention. Triggers may be specific conditions present when (or circumstances under which) a defect is uncovered during testing of software code. As described above, the trigger coverage rule (TCR) tool 35 is operable to determine (or receive determinations of experienced people) the desired coverage rules for the applicable SIT triggers for each connection/interface based on, for example, best practice standards for a particular industry and/or a client's own historical data, (e.g., at the client's option). For example, the TCR tool 35 is operable to apply test coverage rules to systematically capture experience and/or knowledge, as explained below. In accordance with aspects of the invention, this experience and/or knowledge can be applied and reused in a risk-based way.

As shown in FIG. 6, at step 605, the TCR tool receives input "rules" on the needed occurrence numbers for each of the SIT triggers (e.g., coverage, variation, sequencing and interaction, amongst other triggers) at the connection level. These input rules may be determined by resources who are knowledgeable about the system. Additionally, in embodiments the TCR tool may store (e.g., in storage system, 22B of FIG. 1) the determined input rules as templates (e.g., organized by industry and/or technology, etc.) and then load the template directly. At step 610, the TCR tool applies the risk-based testing approach (e.g., accounting for high, medium and low risk connections), as disclosed in related U.S. application Ser. No. 12/558,260, filed on Sep. 11, 2009, to the input rules determined in step 605. For example, in embodiments, the TCR tool may use the result from step 605 for the "medium" connection, increase effort (e.g., more testing) for high risk connections and reduce and/or removing effort (e.g., less or no testing) for low risk connections.

The following is an example of a user-created rule by risk level described in steps 605 and 610 which may be received by the TCR tool. In embodiments, the TCR tool may determine the rule by risk level, e.g., using templates based on an organization's industry and/or technology, etc. For each high risk connection, at least the following SIT testing coverage: two simple coverage (Trigger="Coverage") cases for each of its interfaces; two variant coverage (Trigger="Variation") cases for each of its exceptions; one sequence coverage (Trigger="Sequencing") case for each of its out-bounding sequence interface-to-interface relationships; and one interaction coverage (Trigger="Interaction") case for each of its out-bounding interaction interface-to-interface relationships. For each medium risk connection, at least the following SIT testing coverage: one simple coverage (Trigger="Coverage") case for each of its interfaces; one variant coverage (Trigger="Variation") case for each of its exceptions; and one sequence coverage (Trigger="Sequencing") case for each of its out-bounding sequence interface-to-interface relationships. For each low risk connection, at least the following SIT testing coverage: one simple coverage (Trigger="Coverage") case for each of its interfaces; and one variant coverage (Trigger="Variation") case for each of its exceptions. As should be understood, the above example of the rule by risk level is used for illustrating the present invention and should not be construed as limiting the present invention.

System Integration Test (SIT) Coverage Determination and Method

Figure 7:
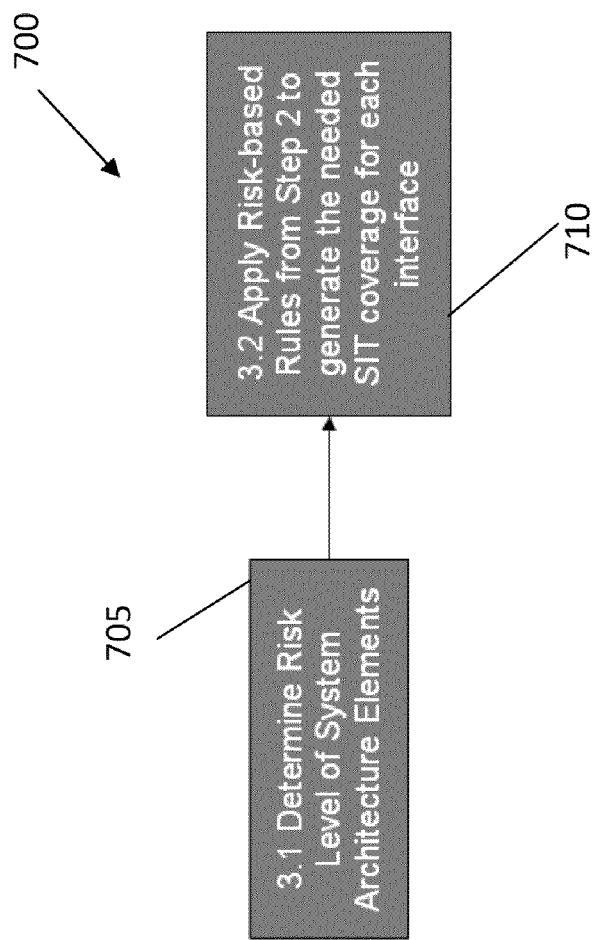

FIG. 7 show an exemplary flow 700 for determining SIT coverage for each connection or interface of the system in accordance with aspects of the invention. As described above, the SIT coverage determination (SCD) tool 40 determines the needed SIT coverage for each connection and interaction of the system. This determination includes, for example, how many simple, variant, sequence, interaction and workload/stress testing occurrences should be executed for each connection and interaction of the system, in accordance with the coverage rules determined by the TCR tool 35.

As shown in FIG. 7, at step 705, the SCD tool 40 determines the risk level (high/low/medium) of the modeling elements (e.g., connections and/or interfaces) in the system architecture model. In embodiments, the risk levels can be manually input by a human (e.g., based on experience, industry, technology) or the risk levels can be determined by applying predefined rules after further annotation on the system architecture model by an expert system, as described in related U.S. application Ser. No. 12/558,260, filed on Sep. 11, 2009. At step 710, the SCD tool applies the risk-based testing occurrence rules to the system architecture model to produce an estimate on how many test cases are needed for each trigger on each modeling element (e.g., interface).

Figure 8:
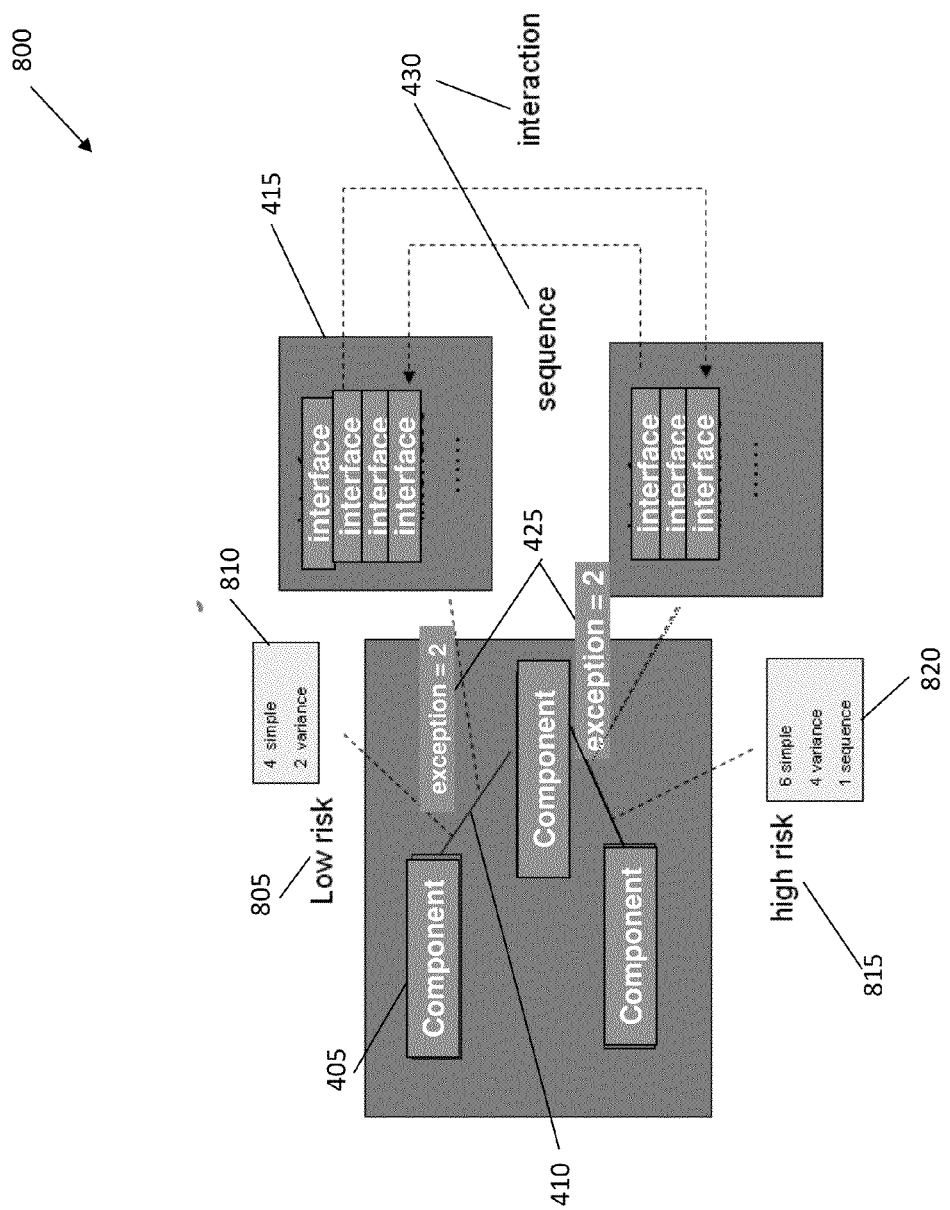
FIG. 8 shows an exemplary illustration of a test case estimate in accordance with aspects of the invention.

FIG. 8 shows an exemplary illustration of a test case estimate 800 produced by the TPOW 100 indicating a number of needed test cases for SIT for two connections by triggers for the exemplary system architecture model 400 illustrated in FIG. 4. As shown in FIG. 8, for each connection 410 or interface 415 between the components 405, the test case estimate 800 indicates a risk level 805 (e.g., high, medium or low). Also, the test case estimate 800 indicates interface/interface relationships 430 (e.g., sequence or interaction) and/or connection exception numbers 425 (e.g., "exception=2").

Additionally, the test case estimate 800 indicates the number of necessary cases by trigger type (e.g., simple, variance, sequence, etc.). For example, for a connection having a high risk 815, the SCD tool determines a number of necessary test cases by trigger type 820. Furthermore, for a connection having a low risk 805, the SCD tool determines a number of necessary cases by trigger type 810. As shown in FIG. 8, the number of test cases for a high risk connection is larger than the number of test cases for the low risk connection. In other words, a high risk connection may warrant more extensive testing than a low risk connection. By identifying those connections that are low risk, lower resources (e.g., less testing) may be allocated to such low risk connections, thus saving costs. Additionally, by identifying those connections that are high risk, higher resources (e.g., more testing) may be allocated to such high risk connections, thus ensuring a return on expenditures for testing. As such, as described by one such implementation above, the SCD tool 40 is operable calculate risk/rule based test case execution requirements for system integration testing (SIT). The SIT test case requirements may be stored in a database (e.g., storage system 22B of FIG. 1).

Figure 9:
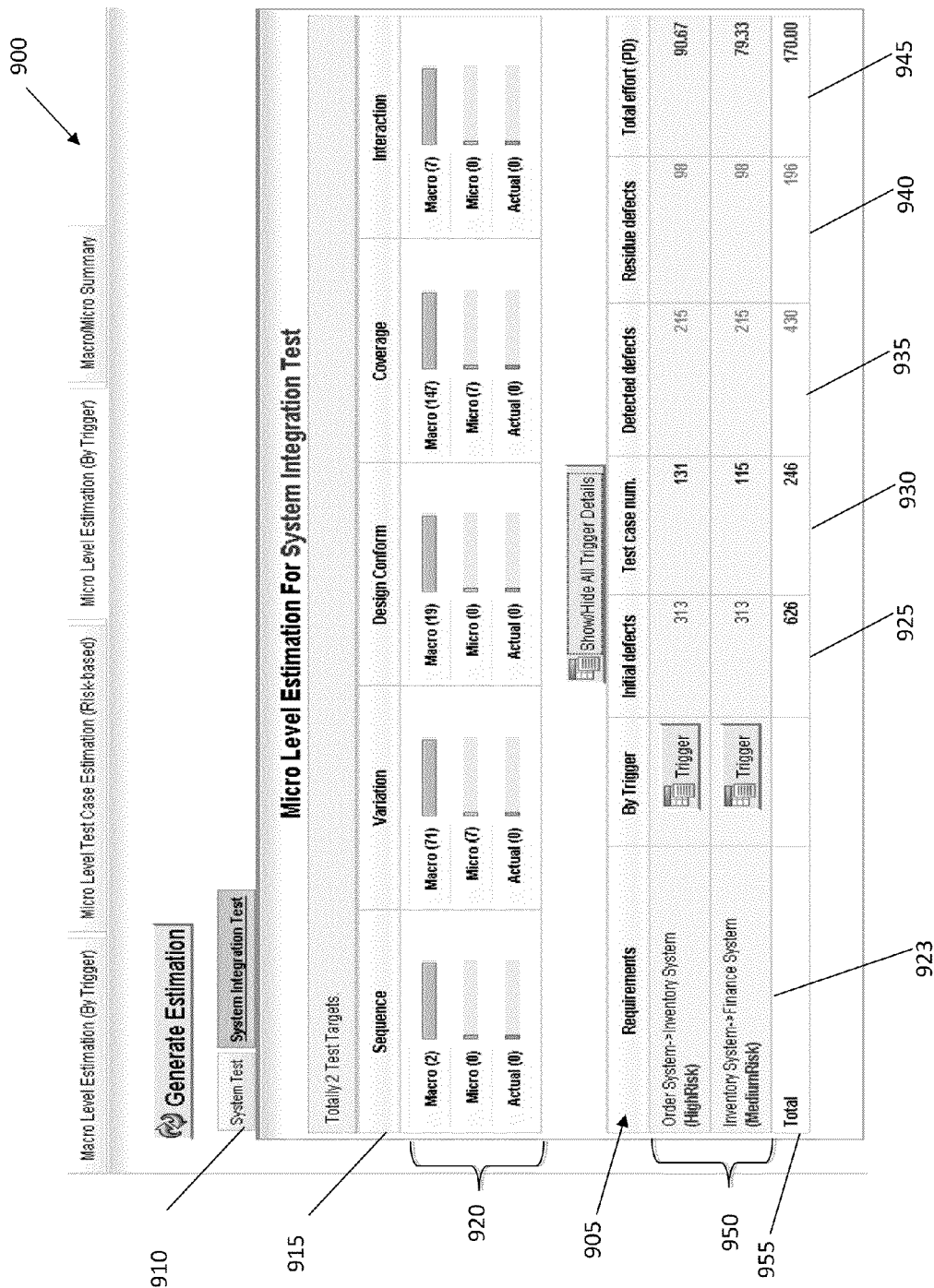
FIG. 9 illustrates an exemplary screenshot of a test case estimate in accordance with aspects of the invention.

FIG. 9 illustrates an exemplary interface and related functionality of a test case estimate 900 produced by the TPOW 100, which indicates a number of needed test cases for SIT for two connections 950 (e.g., order system to inventory system connection, and inventory system to finance system connection) by triggers (listed in row 915). The exemplary test case estimate 900 corresponds with the exemplary user interface 500 (shown in FIG. 5). In embodiments, as shown in FIG. 9, the test case estimate 900 may also include a total effort required (e.g., at the different phases of the software development life cycle) to produce the modeled outcome.

As shown in FIG. 9, table 905 includes a requirements column 923 listing the requirements (e.g., as expressed by a risk factor) for connections or interfaces 950. Additionally, table 905 includes an initial defects column 925 quantifying a number of initial defects (e.g., prior to using the SIT plan determined by the present invention) for each connection in the requirements column 923. A test case number column 930 quantifies a number of test cases required with the SIT plan for each connection in the requirements column 923. A detected defects column 935 quantifies a number of expected defects that will be detected using the generated SIT plan. A residue defects column 940 quantifies the number of expected defects that will escape (e.g., to the production phase of the software development life cycle) using the generated SIT plan. As can be observed, the detected defects and the residue defects will sum to the initial defects for each connection listed in the requirements column 923. Additionally, a total effort column 945 quantifies a total effort (e.g., in person-days or PD) necessary to perform the number of test cases indicated in the test case number column 930. In embodiments, the SCD tool 40 may determine a total effort based on the number of test cases and a cost (in person days) for performing a test case. As can be observed, as the high risk connection uses more test cases than the medium risk connection (e.g., 131 test cases versus 115 test cases), the high risk connection has a larger total effort (e.g., 90.67 versus 79.33). A total row 955 indicates totals for each of columns 925-945. In embodiments, as shown in FIG. 9, the test case estimate 900 may also produce details about expected defect rates in test and production phases (as indicated by tabs 910) of the software development life cycle.

Additionally, as shown in FIG. 9, the test case estimate 900 indicates a number of macro, micro and actual defects 920 for each of the triggers 915 (e.g., sequence, variation, design conformance, coverage and interaction). Macro defects refer to the high level planning/estimation at project initialization phase by comparison with an existing reference project, here shows the top-down test case number estimation based on macro planning effort distribution. In contrast, micro defects refer to the detailed planning/estimation result by analyzing project specific information (e.g., requirements, architecture and etc), here shows the bottom-up micro test case number estimation through annotation. Additionally, as testing occurs, the actual detected defects may be quantified as the actual defects and the SIT coverage may be recalibrated. Actual defects refer to the actual test cases that are used in the real execution (in contrast to the planned number, either macro or micro).

Use Cases Scenario Selection and Method

Figure 10:
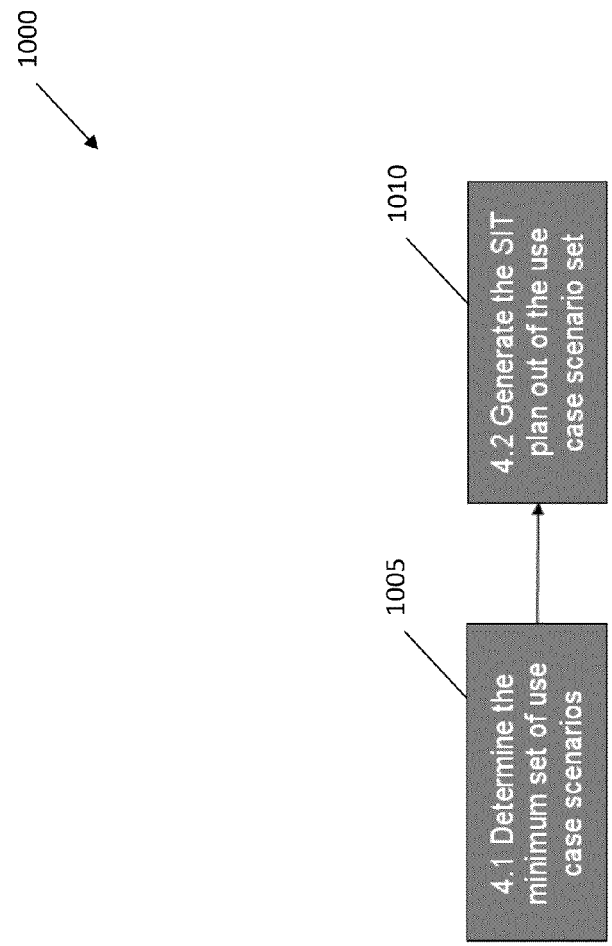
FIGS. 10 and 11 show exemplary flow diagrams in accordance with aspects of the invention.

FIG. 10 show an exemplary flow 1000 for selecting use case scenarios in accordance with aspects of the invention. As described above, the use cases scenario selection (UCSS) tool 45 is operable to generate a minimum set of use cases execution scenarios to satisfy the coverage goal and generate SIT testing design guidelines using the minimum set of use cases execution scenarios. In embodiments, the UCSS tool 35 is operable to combine coverage goals and the type of testing to extrapolate the minimum set of use case execution scenarios while accounting for desired risk levels, as explained below.

Figure 11:
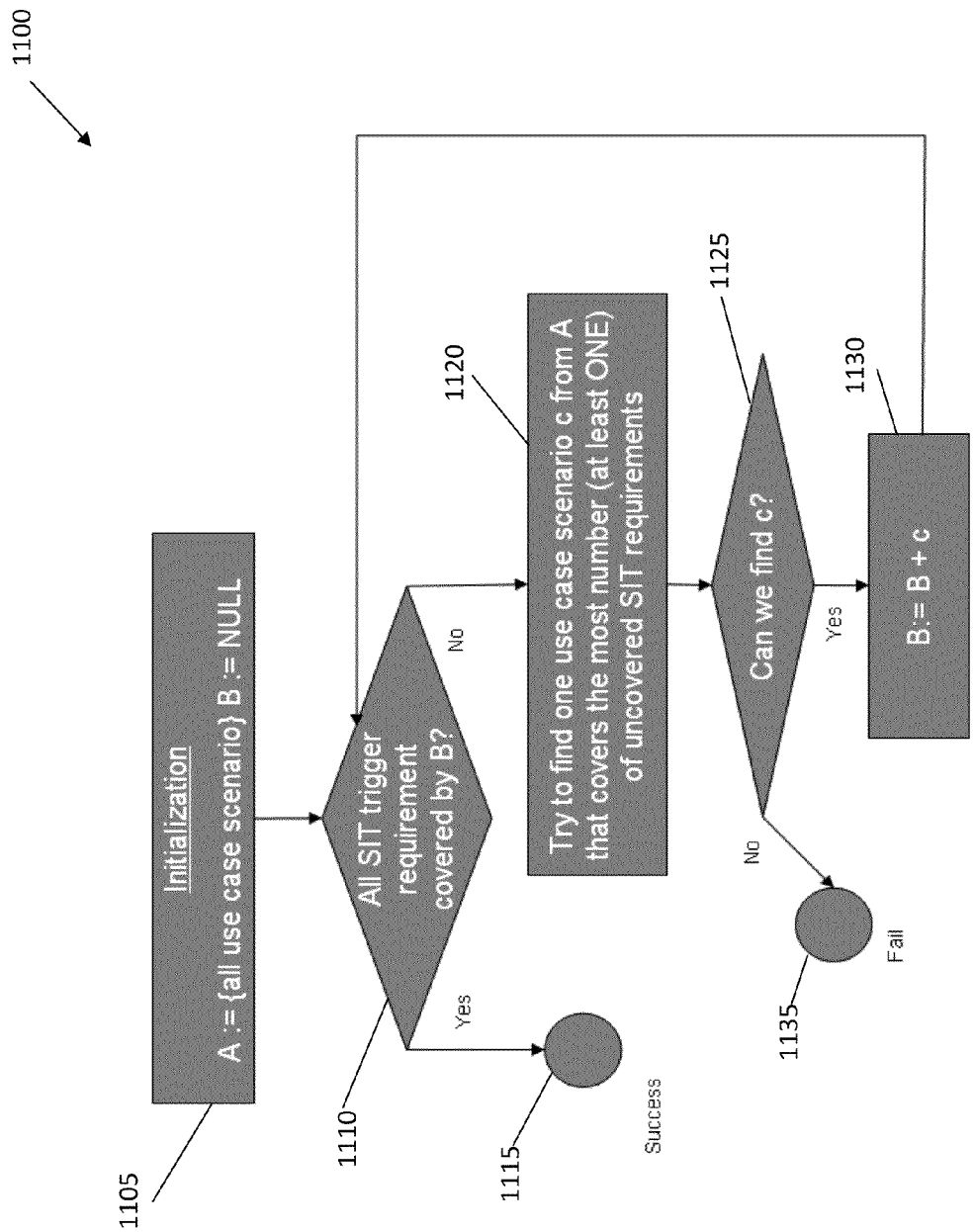

As shown in FIG. 10, at step 1005, the UCSS tool applies an optimization methodology to determine a set of use case scenarios that can cover the needed triggers determined by the SCD tool. In accordance with aspects of the invention, the UCSS tool will determine a minimum number of test cases to be executed while satisfying the entire coverage requirement for each connection/interface. A flow diagram for applying an exemplary optimization methodology to determine a set of use case scenarios that can cover the needed triggers (i.e., performing step 1005) is illustrated in FIG. 11 described below. By reducing the number of test cases to a minimum required to satisfy the needed SIT coverage, the present invention enables a project to, for example, avoid redundant testing and minimize costs. Additionally, in accordance with aspects of the invention, the UCSS tool enables a project, for example, to adjust a set of test cases (e.g., increase a number of test cases) and determine expected results from such adjustments (e.g., an increase in costs and an increase in detected defects).

At step 1010, the UCSS tool generates a SIT plan based on the SIT coverage determination. The SIT test plan can be used, for example, as the guidance for test resources to start designing SIT test cases. In accordance with aspects of the invention, the SIT test cases optimize what is tested by trigger (type of test) and risk, using the system architecture model to ensure no gaps occur in the testing coverage.

FIG. 11 illustrates an exemplary optimization methodology flow diagram 1100 for determining a minimum set of use case scenarios that can cover the needed triggers determined by the SCD tool. As shown in FIG. 11, at step 1105, the UCSS tool initializes, wherein A=all the use case scenarios and B=a minimum set of use case scenarios=Null (or none of the use case scenarios). That is, at step 1105, the minimum set of use case scenarios, B, is initially set to Null and then determined via steps 1110-1135. At step 1110, the UCSS tool determines if all of the SIT trigger requirements (e.g., as determined by the SCD tool) are covered by B. If, at step 1110, the UCSS tool determines that all of the SIT trigger requirements are covered by B, at step 1115, the UCSS tool determines that a minimum set of use case scenarios, B, has been achieved. If, at step 1110, the UCSS tool determines that all of the SIT trigger requirements are not covered by B, then the process proceeds to step 1120. As should be understood, with the first iteration of flow diagram 1100, at step 1110, the determination will be "No" because with the first iteration, B is defined as Null (or none of the use case scenarios).

At step 1120, the UCSS tool examines the use case scenarios to find one use case scenario, "c", from all of the use case scenarios, A, that covers the most (at least one) uncovered SIT requirements. In other words, the UCSS tool searches for a use case scenario that translates to the highest number of SIT test case requirements. At step 1125, the UCSS tool determines whether c exists. If, at step 1125, the UCSS tool determines that c exists, at step 1130, the UCSS tool adds c to the previously determined B to calculate a new B. The process then proceeds to step 1110. If, at step 1125, the UCSS tool determines that c does not exist, at step 1135, the UCSS tool determines a failure has occurred, which indicates that some SIT testing requirements (by triggers) cannot be satisfied by the existing use case scenarios. This usually indicates, for example, that the use case model is not complete (e.g., missing some use cases that would cover some connections by triggers), or the mapping relationship from system architecture to use case model is not well established. In such instances, the use case model may be completed, or the mapping relationship may be better established. Thus, by implementing the present invention, coverage goals and the type of testing (captured by the Trigger element) may be combined to extrapolate a minimum set of use case execution scenarios while accounting for desired risk levels.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims, if applicable, are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principals of the invention and the practical application, and to enable others of ordinary skill in the art to understand the invention for various embodiments with various modifications as are suited to the particular use contemplated. Accordingly, while the invention has been described in terms of embodiments, those of skill in the art will recognize that the invention can be practiced with modifications and in the spirit and scope of the appended claims.

What is claimed is:

1. A method implemented in a computer infrastructure having computer executable code tangibly embodied on a computer readable storage medium having programming instructions operable to:
   receive a system architecture model of a system using a processor, wherein the receiving the system architecture model comprises:
      determining whether the system architecture model exists;
      importing the system architecture model when determined to exist;
      when the system architecture model is determined to not exist:
         identifying and capturing a components model of the system architecture model;
         identifying and capturing a connections model of the system architecture model; and
      refining the connections model into interface models;
      annotating the system architecture model; and
      mapping from the system architecture model to one or more use case models;
   receive trigger coverage rules;
   determine system integration test (SIT) coverage for each connection and interface of the system architecture model; and
   select a set of use cases execution scenarios to satisfy the SIT coverage.

2. The method of claim 1, wherein the components model comprises at least one of a system, a sub system and a module of the system architecture model.

3. The method of claim 1, wherein the connection model comprises at least one of a connection and an interface between components of the system architecture model.

4. The method of claim 1, wherein the one or more use case models represent business functions of the system.

5. A method implemented in a computer infrastructure having computer executable code tangibly embodied on a computer readable storage medium having programming instructions operable to:
   receive a system architecture model of a system using a processor;
   receive trigger coverage rules;
   determine system integration test (SIT) coverage for each connection and interface of the system architecture model; and
   select a set of use cases execution scenarios to satisfy the SIT coverage,
   wherein the receiving the trigger coverage rules comprises:
      receiving projected occurrence frequencies for each of a plurality of SIT triggers for each connection and interface of the system architecture model; and
      determining one or more rules for adjusting the projected occurrence frequencies based on one or more risk levels.

6. The method of claim 5, wherein: the one or more risk levels is one of high risk, medium risk, and low risk, wherein the medium risk ranges between the high risk and the low risk, and the determining one or more rules for adjusting the one or more of the projected occurrence frequencies comprises: increasing a projected occurrence frequency for a connection having a high risk; and decreasing a projected occurrence frequency for a connection having a low risk.

7. The method of claim 5, wherein the plurality of SIT triggers comprise at least one of coverage, variation, sequencing and interaction.

8. The method of claim 5, wherein the determining the system integration test (SIT) coverage for each connection and interface of the system architecture model comprises:
   determining a risk level of one or more connections of the system architecture model; and
   adjusting the projected occurrence frequencies for each of a plurality of SIT triggers for each connection and interface of the system architecture model based on the risk level of the one or more connections.

9. The method of claim 1, wherein the selecting the set of use case execution scenarios to satisfy the SIT coverage comprises selecting a minimum set of use case execution scenarios to satisfy the SIT coverage.

10. The method of claim 9, wherein selecting the minimum set of use case execution scenarios to satisfy the SIT coverage, comprises:
    determining a minimum set of use case execution scenarios; and
    generating an SIT plan from the minimum set of use case execution scenarios.

11. A method implemented in a computer infrastructure having computer executable code tangibly embodied on a computer readable storage medium having programming instructions operable to:
    receive a system architecture model of a system using a processor;
    receive trigger coverage rules;
    determine system integration test (SIT) coverage for each connection and interface of the system architecture model; and
    select a set of use cases execution scenarios to satisfy the SIT coverage,
    wherein the selecting the set of use case execution scenarios to satisfy the SIT coverage comprises selecting a minimum set of use case execution scenarios to satisfy the SIT coverage;
    wherein determining the minimum set of use case execution scenarios comprises:
       setting the minimum set of use case execution scenarios to a null set;
       detecting a use case scenario from a plurality of use case scenarios which covers a highest number of uncovered SIT trigger requirements;
       adding the use case scenario to an intermediate set of use case execution scenarios;
       determining whether the intermediate set of use case execution scenarios satisfies the SIT coverage; and
    wherein:
       when the intermediate set of use case execution scenarios satisfies the SIT coverage, setting the intermediate set of use case execution scenarios as the minimum set of use case execution scenarios; and
when the intermediate set of use case execution scenarios does not satisfy the SIT coverage, reverting to the detecting.

12. The method of claim 1, wherein a service provider at least one of creates, maintains, deploys and supports the computer infrastructure.

13. The method of claim 1, wherein steps are provided by a service provider on a subscription, advertising, and/or fee basis.

14. A system implemented in hardware, comprising: a system architecture model acquisition (SAMA) tool, implemented in a processor, operable to receive a system architecture model of a system, wherein the receiving the system architecture model comprises: determining whether the system architecture model exists; importing the system architecture model when determined to exist: when the system architecture model is determined to not exist: identifying and capturing a components model of the system architecture model; identifying and capturing a connections model of the system architecture model; and refining the connections: model into interface: models; annotating the system architecture model: and mapping from the system architecture model to one or more use case models; a trigger coverage rule (TCR) tool operable to receive trigger coverage rules; a system integration test (SIT) coverage determination tool operable to determine SIT trigger coverage for each connection and interface of the system architecture model; and a use case scenario selection (UCSS) tool operable to select a set of use cases execution scenarios to satisfy the SIT trigger coverage.

15. The system of claim 14, wherein:
the components model comprises at least one of a system, a sub system and a module of the system architecture model;
the connection model comprises at least one of a connection and an interface between components of the system architecture model; and
the one or more use case models represent business functions of the system.

16. A system implemented in hardware, comprising: a system architecture model acquisition (SAMA) tool, implemented in a processor, operable to receive a system architecture model of a system; a trigger coverage rule (TCR) tool operable to receive trigger coverage rules: a system integration test (SIT) coverage determination tool operable to determine SIT trigger coverage for each connection and interface of the system architecture model: and a use case scenario selection (UCSS) tool operable to select a set of use cases execution scenarios to satisfy the SIT trigger coverage, wherein the receiving the trigger coverage rules comprises: receiving projected occurrence frequencies for each of a plurality of SIT triggers for each connection and interface of the system architecture model; and determining one or more rules for adjusting the projected occurrence frequencies based on one or more risk levels.

17. The system of claim 16, wherein: the one or more risk levels is one of high risk, medium risk and low risk, wherein the medium risk ranges between the high risk and the low risk, and the determining one or more rules for adjusting the one or more of the projected occurrence frequencies comprises: increasing a projected occurrence frequency for a connection having a high risk; and decreasing a projected occurrence frequency for a connection having a low risk.

18. The system of claim 16, wherein the plurality of SIT triggers comprise at least one of coverage, variation, sequencing and interaction.

19. A system implemented in hardware, comprising: a system architecture model acquisition (SAMA) tool, implemented in a processor, operable to receive a system architecture model of a system: a trigger coverage rule (TCR) tool operable to receive trigger coverage rules; a system integration test (SIT) coverage determination tool operable to determine SIT trigger coverage for each connection and interface of the system architecture model: and a use case scenario selection (UCSS) tool operable to select a set of use cases execution scenarios to satisfy the SIT trigger coverage, wherein, wherein the determining the system integration test (SIT) coverage for each connection and interface of the system architecture model comprises: determining a risk level of one or more connections of the system architecture model; and adjusting the projected occurrence frequencies for each of a plurality of SIT triggers for each connection and interface of the system architecture model based on the risk level of the one or more connections.

20. The system of claim 14, wherein the selecting the set of use case execution scenarios to satisfy the SIT coverage comprises selecting a minimum set of use case execution scenarios to satisfy the SIT coverage, comprising:
determining a minimum set of use case execution scenarios; and
generating an SIT plan from the minimum set of use case execution scenarios.

21. A computer program product comprising a computer readable storage medium having readable program code embodied in the storage medium, the computer program product includes at least one component operable to: receive a system architecture model of a system, using a processor wherein the system architecture model comprises: a components model comprising at least one of a system, a sub system and a module of the system architecture model; a connection model comprising at least one of a connection and an interface between components of the system architecture model; and one or more use case models represent business functions of the system; receive trigger coverage rules; determine system integration test (SIT) coverage for each connection and interface of the system architecture model; and select a minimum set of use cases execution scenarios to satisfy the SIT coverage wherein: the receiving the trigger coverage rules comprises: receiving projected occurrence frequencies for each of a plurality of SIT triggers for each connection and interface of the system architecture model: and determining one or more rules for adjusting the projected occurrence frequencies based on one or more risk levels, wherein: the one or more risk levels is one of high risk, medium risk and low risk wherein the medium risk ranges between the high risk and the low risk; and the determining one or more rules for adjusting the one or more of the projected occurrence frequencies comprises: increasing a projected occurrence frequency for a correction having a high risk; and decreasing a projected occurrence frequency for a connection having a low risk; and the determining the system integration test (SIT) coverage for each connection and interface of the system architecture model comprises: determining a risk level of one or more connections of the system architecture model; and adjusting the projected occurrence frequencies for each of a plurality of SIT triggers for each connection and interface of the system architecture model based on the risk level of the one or more connections.

* * * * *